(12) United States Patent
Graham

(10) Patent No.: US 6,200,610 B1
(45) Date of Patent: Mar. 13, 2001

(54) CODED TRACER FOR ANIMAL FEEDS

(76) Inventor: Ronald C. Graham, P.O. Box 419, Acme, Alberta (CA), T0M 0A0

( * ) Notice: Subject to any disclaimer, the term of this patent is extended or adjusted under 35 U.S.C. 154(b) by 0 days.

(21) Appl. No.: 09/462,828

(22) PCT Filed: Jan. 5, 1998

(86) PCT No.: PCT/CA98/00005

§ 371 Date: Jan. 14, 2000

§ 102(e) Date: Jan. 14, 2000

(87) PCT Pub. No.: WO99/04259

PCT Pub. Date: Jan. 28, 1999

(30) Foreign Application Priority Data

Jul. 17, 1997 (CA) .................................................. 2209035

(51) Int. Cl.[7] ........................... G01N 33/02; G01N 21/29
(52) U.S. Cl. ........................... 426/87; 426/132; 426/231; 426/250; 426/302; 426/807
(58) Field of Search .............. 426/87, 132, 231, 426/250, 302, 807

(56) References Cited

U.S. PATENT DOCUMENTS

| | | | |
|---|---|---|---|
| 2,685,517 | * 8/1954 | Dunmire | 99/11 |
| 2,868,644 | * 1/1959 | Eisenberg | 99/2 |
| 3,438,781 | * 4/1969 | MacMillan et al. | 99/2 |
| 3,469,990 | * 9/1969 | Eisenberg | 99/2 |
| 4,029,820 | * 6/1977 | Eisenberg | 426/74 |
| 4,188,408 | * 2/1980 | Eisenberg | 426/74 |
| 4,421,858 | * 12/1983 | Jackson | 436/20 |
| 4,654,165 | * 3/1987 | Eisenberg | 252/408.1 |
| 4,861,586 | * 8/1989 | Schneider et al. | 424/84 |

FOREIGN PATENT DOCUMENTS

383116 * 8/1990 (EP) .

OTHER PUBLICATIONS

McIlhiney et al. Anim. Feed Sci. Technol. vol. 8, No. 2, pp. 139–146, 1983.*

* cited by examiner

Primary Examiner—Chhaya D. Sayala

(57) ABSTRACT

A batch identifier for seeds and livestock feeds in the form of coded particles of approximately the same size as the seed or feed is disclosed. In use the coded particles are mixed with the seed or feed. The batch identifier may be paper or plastic, and coated or uncoated; and the coding may be any appropriate symbols such as letters or numbers.

13 Claims, 1 Drawing Sheet

CODED TRACER FOR ANIMAL FEEDS

FIELD OF THE INVENTION

This invention relates to a batch identifier for use in seeds and animal feeds.

BACKGROUND OF THE INVENTION

The food that farmers provide to livestock often includes prepared feeds. These prepared feeds may be as simple as milled grains, but they often comprise several ingredients including minute quantities of supplements such as vitamins and minerals. With some prepared feeds, the various ingredients are merely mixed together, but in other prepared feeds the ingredients are mixed and then formed into pellets, which typically involves the application of steam to the ingredients.

It is common in tracers for use in animal feeds to utilize inert chemical compounds which can be easily mixed with other ingredients and analysed for in samples, and also compounds of which the ingredients would have low levels, such that there would be low background levels. Another type of tracer utilizes colouring, either an ingredient which colours the entire feed product or small particles which are colour-coated and detectable by release of the colour with a solvent. These disclosed tracers are useful for determining the concentration of ingredients in a sample of feed, but they are of no use when it is necessary to distinguish between different batches of a particular prepared feed. Tracers of these types are limited in the scope of application because detection may be difficult when the tracer is diluted, and without a means of uniquely coding the tracer, consecutive batches of feed can not be differentiated.

In the feed industry, as standards of quality rise, and as public expectations of quality also rise, strict quality control management becomes more and more important, for example, the ability of the manufacturer to recall a specific batch if there is an error in mixing. The invention of a tracer which is readily detectable and coded, such that individual batches of feed products can be differentiated, will facilitate quality control procedures in the processing and distribution of such feed products.

SUMMARY OF THE INVENTION

According to one aspect, the invention consists of a batch identifying system comprising a plurality of marker sets, wherein each marker set comprises a plurality of markers and each marker in a marker set bears an identifying indicium which is the same within a marker set but different from other sets, and further wherein a marker set is mixed with a batch of seed or feed to distinguish the batch from other batches.

The markers may be of the approximate size of the constituents of the seed or feed. The markers may be plastic. The markers may be paper. The markers may have a coating. The coating may be wax. The coating may be a resin.

The identifying indicium may be one or more symbols on the markers. The symbols may be letters. The symbols may be numerals. The symbols may be letters and numerals. The identifying indicium may also be colour on the markers.

According to another aspect, the invention consists of a method for identifying batches of seed or feed, which comprises:

(a) mixing a set of markers having an identifying indicium for differentiating that set of markers from other sets of markers, into a batch of seed or feed;

(b) making a record of the identifying indicium and the batch of seed or feed;

(c) viewing a marker in the seed or feed; and (d) comparing the identifying indicium of the viewed marker with the record.

Viewing the marker may consist of viewing a sample of the seed or feed under magnification to locate the marker and to identify the identifying indicium.

BRIEF DESCRIPTION OF THE DRAWING

In drawings which illustrate embodiments of the invention.

DETAILED DESCRIPTION

Figure 1:
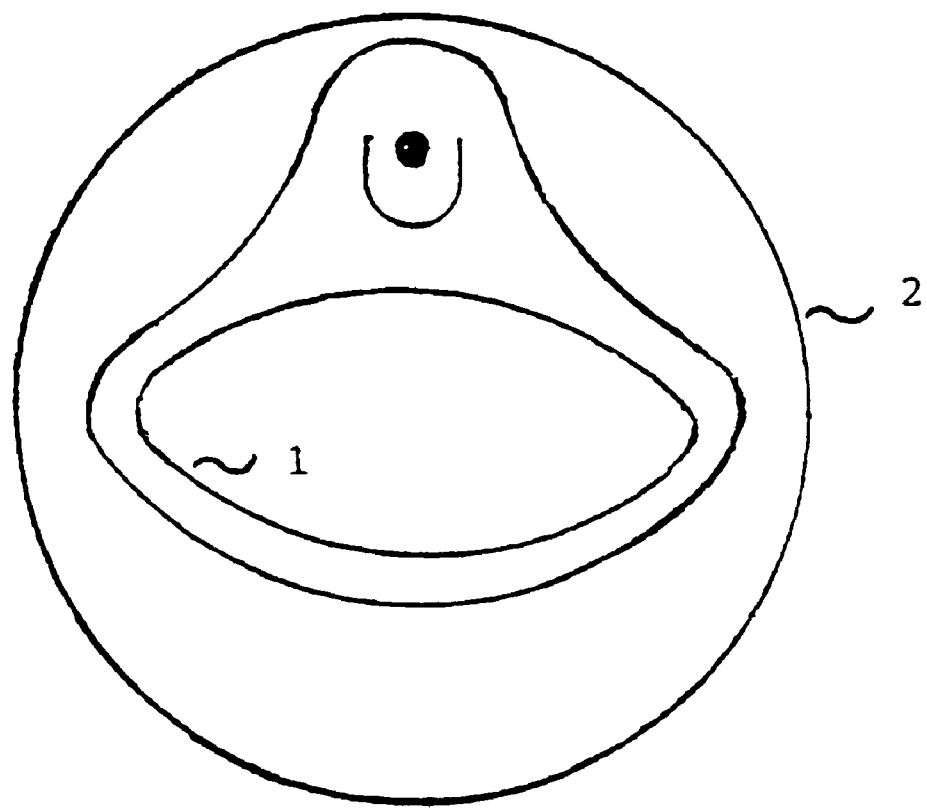
FIG. 1 is an enlarged plan view of an individual tracer particle among adjacent particles of feed ingredients.

Definitions:

In this patent application:

(a) "seed or feed" is used to mean either prepared livestock feeds or seeds; and (b) "batch" is used to mean a batch, production run, lot, shipment or any other group of seed or feed where it may be useful to differentiate one such group from another.

In this invention, the batch identifier consists of uniformly sized particles, made of paper products, including cardboard, or plastic products, serving as a harmless marker, of which a very small amount is included in a quantity of the animal feed. The particle size of the markers may approximate the particle size of the feed ingredients, in the intended use, as is necessary to have adequate mixing.

In the embodiment shown in FIG. 1, the marker (1) is approximate in size to the adjacent feed particles (2). The batch identifier, for a specific application, would have markers (1) of uniform size and shape, but the size and shape used would depend on the application and would commonly range from 0.001 to 1000 cubic millimeters.

The batch identifiers are distinguishable by identifying indicium, such as colouring and by coding on the tracer particles. The code may consist of a group of symbols, such as numbers and letters, so that the markers used in a single batch of feed would all have the same code, which would be different from that of the tracer used in other batches. For the convenience of the consumer, the markers could be differently coloured for various feed product types, and coded to indicate the manufacturing company and the sequential batch number.

The batch identifier would usually be included into a quantity of feed within a range of rates of 0.1 to 1000 grams of markers to 1000 kilograms of feed. The markers would usually be premixed with a carrier ingredient prior to mixing with the quantity of feed, to facilitate efficient mixing and distribution of the markers.

The markers would usually withstand normal processing procedures and remain stable in normal storage conditions adequate for the feed products. The markers may be improved by a coating on the markers of an appropriate resin or wax product, especially for certain applications, such as with the inclusion of liquid feed ingredients or of steam.

The detection and observation of the markers in samples of the feed may be done by a microscopic inspection of the sample, and usually magnification of approximately 25 to 35 times is adequate. In feeds that have been pelleted or similarly processed, the sample may be crushed to separate the ingredient particles to facilitate the inspection.

Another way in which this invention may be used is as a batch identifier in plant seeds, such as in agricultural applications, for similar purposes as with animal feeds, to mark and track batches of seed.

Another way in which this invention may be used is in the testing of the mixing ability of mixing equipment, by quantitative measurement of markers per unit of weight in consecutive samples from a batch of feed.

What is claimed is:

1. A batch identifying system comprising a plurality of marker sets, wherein each marker set comprises a plurality of markers and each marker in a marker set bears an identifying indicium which is the same within a marker set but different from other sets, and further wherein a marker set is mixed with a batch of seed or feed to distinguish the batch from other batches.

2. The batch identifying system of claim 1 wherein the markers are of the approximate size of the constituents of the seed or feed.

3. The batch identifying system of claim 1 wherein the markers are plastic.

4. The batch identifying system of claim 1 wherein the markers are paper.

5. The batch identifying system of claim 4 wherein the markers have a coating.

6. The batch identifying system of claim 5 wherein the coating is wax.

7. The batch identifying system of claim 5 wherein the coating is a resin.

8. The batch identifying system of claim 1 wherein the identifying indicium comprises one or more symbols on the markers.

9. The batch identifying system of claim 8 wherein said symbols comprise letters.

10. The batch identifying system of claim 8 wherein said symbols comprise numerals.

11. The batch identifying system of claim 8 wherein the identifying indicium further comprises colour on the markers.

12. A method of identifying batches of seed or feed, which comprises:

(a) mixing a set of markers having an identifying indicium for differentiating that set of markers from other sets of markers, into a batch of seed or feed;

(b) making a record of the identifying indicium and the batch of seed or feed;

(c) viewing a marker in the seed or feed; and (d) comparing the identifying indicium of the viewed marker with the record.

13. The method of claim 12, wherein viewing the marker comprises viewing a sample of the seed or feed under magnification to locate the marker and to identify the identifying indicium.

\* \* \* \* \*